United States Patent
Effertz

(10) Patent No.: US 6,887,827 B2
(45) Date of Patent: May 3, 2005

(54) COMBINATIONS OF HERBICIDAL AROMATIC CARBOXYLIC ACIDS AND SAFENERS

(75) Inventor: Chad Effertz, Velva, ND (US)

(73) Assignee: Bayer CropScience GmbH, Frankfurt am Main (DE)

(*) Notice: Subject to any disclaimer, the term of this patent is extended or adjusted under 35 U.S.C. 154(b) by 0 days.

(21) Appl. No.: 10/456,564

(22) Filed: Jun. 5, 2003

(65) Prior Publication Data

US 2003/0232725 A1 Dec. 18, 2003

(30) Foreign Application Priority Data

Aug. 6, 2002 (EP) .............................. 02012766

(51) Int. Cl.$^7$ .............................................. A01N 25/32
(52) U.S. Cl. ...................... 504/105; 504/106; 504/109; 504/110; 504/112; 504/324
(58) Field of Search ................................ 504/105, 106, 504/109, 110, 112, 324

(56) References Cited

U.S. PATENT DOCUMENTS

| | | | |
|---|---|---|---|
| 2,848,470 A | 8/1958 | Girard et al. ............... | 260/429 |
| 3,013,054 A | 12/1961 | Richter ...................... | 260/473 |
| 3,014,063 A | 12/1961 | McLane et al. ............. | 260/471 |
| 3,081,162 A | 3/1963 | Tischler et al. ............... | 71/2.6 |
| 5,201,933 A * | 4/1993 | Miller et al. ................. | 504/104 |
| 6,235,680 B1 | 5/2001 | Ziemer et al. ............... | 504/112 |
| 2002/0055435 A1 * | 5/2002 | Baltruschat et al. ......... | 504/103 |

FOREIGN PATENT DOCUMENTS

| | | |
|---|---|---|
| EP | 0 480 902 A1 | 4/1992 |
| EP | 0 795 269 A1 | 9/1997 |
| WO | WO 97/45016 | 12/1997 |
| WO | WO 98/13361 | 4/1998 |
| WO | WO 98/47356 | 10/1998 |
| WO | WO 02/060255 A2 | 8/2002 |

OTHER PUBLICATIONS

Tokyo Research Lab., vol. 24, No. 3, 1979, pp. 194–198, also referred to as XP001118547.

L.D. Knerr et al., "Naptalam as a Safener Against Chloramben in Cucumber", Tokyo Res. Lab., vol. 24, No. 3, pp. 194–198, 1979 (referred to as XP–002217599).

* cited by examiner

Primary Examiner—S. Mark Clardy
(74) Attorney, Agent, or Firm—Frommer Lawrence & Haug LLP

(57) ABSTRACT

Combinations of herbicidal aromatic carboxylic acids and safeners

The invention relates to a herbicide-safener combination, which comprises:
(A) one or more herbicidal auxin type of aromatic carboxylic acids or salts thereof, for example dicamba, chloramben or 2,3,6-trichlorobenzoic acid (2,3,6-TBA), and
(B) one or more safeners selected from the group consisting of:
(B1) active compounds of the heterocyclic carboxylic acid type and their derivatives, preferably their esters or salts, selected from the group consisting of
  (B1.1) compounds of the phenylpyrazolin-3-carboxylic acid type,
  (B1.2) derivatives of the phenylpyrazolecarboxylic acid type,
  (B1.3) compounds of the triazolecarboxylic acid type,
  (B1.4) compounds of the 5-benzyl-, 5-phenyl- or 5,5-diphenyl-2-isoxazoline-3-carboxylic acid type,
  (B1.5) flurazole and
  (B1.6) dimepiperate,
(B2) active compounds, or salts thereof, which, in addition to a herbicidal action against harmful plants, also have a safener action in crop plants such as rice, selected from the group consising of
  (B2.1) daimuron
  (B2.2) cumyluron
  (B2.3) methoxyphenone and
  (B2.4) CSB
(B3) safening active N-acylsulfonamides selected from the group consisting of
  (B3.1) N'-acyl-N-benzoyl-aminobenzolsulfonamides or their salts
  (B3.2) acylsulfamoylbenzamides or salts thereof, with the exception of herbicide-safener combinations comprising dicamba or salts thereof and a safener selected from the group (B1.4) defined above. The invention is also directed to the respective method for protecting crops, the method for weed control using the combination and the use of compounds (B) for safening compounds (A).

19 Claims, No Drawings

COMBINATIONS OF HERBICIDAL AROMATIC CARBOXYLIC ACIDS AND SAFENERS

The invention relates to the technical field of crop protection compositions, in particular combinations of the auxin type of herbicidal aromatic carboxylic acids and safeners, especially combinations of the herbicides dicamba, chloramben or 2,3,6-trichlorobenzoic acid (2,3,6-TBA) and safeners, which are highly suitable for use against harmful plants in crops of useful plants.

Herbicidally active compounds from the auxin type of aromatic carboxylic acids, have good use properties and can be employed at relatively low application rates against a range of gramineous and/or broad-leaved weeds; cf. U.S. Pat. No. 3,013,054, U.S. Pat. No. 3,014,063, U.S. Pat. No. 3,174,842, U.S. Pat. No. 3,081,162 and U.S. Pat. No. 2,848,470. However, these compounds are not always fully compatible with some important crop plants, such as the cereals wheat, barley, rice, maize and sorghum, or dicotyledonous crops, such as soya bean, sunflower and sugar cane, (including transgenic selective herbicide tolerant varieties such as glufosinate tolerant varieties, for example ®Liberty link corn, or glyphosate tolerant varieties, for example ®Round-up-ready corn or soybean) so that their use as selective herbicides is in some instances limited. The herbicides can in this case only be used, if at all, at application rates which are compatible with the crops and so low that the desired broad herbicidal action against harmful plants is not ensured.

It is known that many herbicides injure crop plants at herbicide application rates needed to control weed growth. This renders many herbicides unsuitable for controlling weeds in the presence of certain crops. Where weed growth in crops is uncontrolled however, this results in lower crop yield and reduced crop quality, as weeds will compete with crops for nutrients, light and water. Reduction in herbicidal injury to crops without an unacceptable reduction in the herbicidal action can be accomplished by use of crop protectants known as "safeners", also sometimes referred to as "antidotes" or "antagonists". The safening effect of a compound is generally specific to the herbicidal partner and the crop where the active ingredients are applied.

It is already known from EP-A-0480902 to reduce phytotoxicity of benzoic acid type herbicides on crops by the addition of some safeners of the dichloroacetamide type and various other safeners.

EP-A-0795269 describes the combination of cloquintocet-mexyl or similar safeners of the quinolinoxyacetate type for reducing phytotoxicity of dicamba on crops.

WO 98/47356 relates to combinations of dicamba and specific dichloroacetamide safeners having heterocyclic rings, such as furilazole, benoxacor, AD 97 or specific dicarboxylic acid safeners having heterocyclic rings such as CL 304415=2-(4-carboxychroman-4-yl)acetic acid.

We have now shown that, surprisingly, crop plants can be effectively protected against undesirable damage by specific herbicides if the herbicides are applied together with certain compounds acting as safeners (herbicide antidotes) to the crop plants.

Accordingly, the present invention provides herbicide-safener combinations, for example in the form of preparations for use as herbicidal compositions, comprising:
(A) one or more herbicidal auxin type aromatic carboxylic acids or agriculturally acceptable salts thereof; for example selected from the group consisting of:
(A1) 3,6-dichloro-2-methoxybenzoic acid (dicamba) or its salts, preferably dicamba, dicamba-dimethylammonium, dicamba-potassium, dicamba-sodium or dicamba-diolamine,
(A2) 3-amino-2,5-dichlorobenzoic acid (chloramben) or its salts, and
(A3) 2,3,6-trichlorobenzoic acid (2,3,6-TBA) or its salts, and
(B) one or more safeners selected from the group consisting of:
(B1) active compounds of the heterocyclic carboxylic acid type and their derivatives, preferably their esters or salts, selected from the group consisting of
(B1.1) compounds of the phenylpyrazolin-3-carboxylic acid type,
(B1.2) derivatives of the phenylpyrazolecarboxylic acid type,
(B1.3) compounds of the triazolecarboxylic acid type,
(B1.4) compounds of the 5-benzyl-, 5-phenyl- or 5,5-diphenyl-2-isoxazoline-3-carboxylic acid type,
(B1.5) flurazole and
(B1.6) dimepiperate,
(B2) active compounds, or salts thereof, which, in addition to a herbicidal action against harmful plants, also have a safener action in crop plants such as rice, selected from the group consising of
(B2.1) daimuron
(B2.2) cumyluron
(B2.3) methoxyphenone and
(B2.4) CSB
(B3) safening active N-acylsulfonamides selected from the group consisting of
(B3.1) N'-acyl-N-benzoyl-aminobenzolsulfonamides or their salts
(B3.2) acylsulfamoylbenzamides or salts thereof,
with the exception of herbicide-safener combinations comprising dicamba or salts thereof and a safener selected from the group (B1.4) defined above.

The safeners (B) used in the combinations of the present invention are understood to embrace all stereoisomers and mixtures thereof, as well as their salts.

Some of the safeners are known as herbicidally active compounds, and accordingly, in addition to the herbicidal action on harmful plants, they also have a protective effect on the crop plants.

The advantageous safener effects are observed when the active compounds (A) and (B) are applied simultaneously, however, they can also frequently be observed when the active compounds are applied at different times (splitting). It is also possible to apply the active compounds in a plurality of portions (sequential application), for example after pre-emergence applications, followed by post-emergence applications or after early post-emergence applications, followed by medium or late post-emergence applications. It is also possible to use the safeners as a dressing for pre-treating the seeds of the crop plants or plant seedlings.

The active compounds of the combination in question are preferably supplied jointly or within a short interval.

The herbicide-safener combinations reduce or eliminate phytotoxic effects which can occur when the herbicidally active compounds (A) are used in useful plants, without having any substantial detrimental effect on the activity of these active compounds against harmful plants. They permit a higher dosage (application rate) of the herbicide compared to the individual application of the herbicide in crops of useful plants, and thus a more effective control of the competing harmful plants. The higher efficacy permits the control of species which are as yet uncontrolled (gaps), an extension of the period of application and/or a reduction in the number of individual applications required and—as a result for the user—weed control systems which are more advantageous economically and ecologically.

It has hitherto not been known and is also surprising that the phytotoxicity of the herbicidal aromatic carboxylic acids (A) can be reduced effectively or eliminated with the aid of safeners (B). In general, the herbicidal aromatic carboxylic acids have an activity profile which is different from that known of other classes of herbicidally active compounds. Thus, an effect of the safeners in combination with herbicidal aromatic carboxylic acids has not been disclosed yet and could not have been predicted in a similar fashion.

Dicamba (A1) or a salt thereof is a preferred herbicide (A) for the herbicide-safener combinations.

The herbicidal aromatic carboxylic acids (A) are known. The preparation of such compounds is described, for example, in the above mentioned publications, or can be carried out, for example by or analogously to the methods described in these publications.

For the preferred compounds, their preparation and general conditions for their use and in particular for specific example compounds, reference is made to the descriptions of the publications mentioned, and these descriptions are also part of the present invention.

The compounds of the formula (I) can form salts by addition of a suitable inorganic or organic acid, such as, for example, HCl, HBr, $H_2SO_4$ or $HNO_3$, but also oxalic acid or sulfonic acids, to a basic group, such as, for example, amino or alkylamino. Suitable substituents which are present in deprotonated form, such as, for example, sulfonic acids or carboxylic acids, can form inner salts with groups which for their part can be protonated, such as amino groups. Salts can also be formed by replacing the hydrogen of suitable substituents, such as, for example, sulfonic acids or carboxylic acids, by an agriculturally suitable cation. These salts are, for example, metal salts, in particular alkali metal salts or alkaline earth metal salts, in particular sodium salts and potassium salts, or else ammonium salts, salts with organic amines or quaternary ammonium salts.

In the formula (I) and all the formulae hereinbelow, the radicals alkyl, alkoxy, haloalkyl, haloalkoxy, alkylamino and alkylthio and the corresponding unsaturated and/or substituted radicals can in each case be straight-chain or branched in the carbon skeleton. Unless specifically mentioned otherwise, the lower carbon skeletons, for example with 1 to 6 carbon atoms or in the case of unsaturated groups with 2 to 6 carbon atoms are preferred for these radicals. Alkyl radicals, also in the composed meanings, such as alkoxy, haloalkyl, and the like, are, for example, methyl, ethyl, n- or isopropyl, n-, i-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methyl-but-3-en-1-yl and 1-methyl-but-2-en-1-yl; alkynyl is, for example, propargyl, but-2-yn-1-yl, but-3-yn-1-yl, 1-methylbut-3-yn-1-yl.

A hydrocarbon radical is a straight-chain, branched or cyclic unsaturated or saturated aliphatic or aromatic hydrocarbon radical, such as alkyl, alkenyl, alkynyl, cycloalkyl, cycloalkenyl or aryl, preferably alkyl, alkenyl or alkynyl having preferably up to 12 carbon atoms or cycloalkyl having 3 to 6 ring atoms or phenyl, the same applies analogously to a hydrocarbon-oxy or hydrocarbon-thio radical.

Alkylidene, for example in the form $(C_1–C_{10})$-alkylidene, is the radical of a straight-chain or branched alkane which is attached via a double bond, the position of the binding site not yet being fixed. In the case of a branched alkane, the only possible positions are, of course, those where two hydrogen atoms can be replaced by the double bond; examples of radicals are $=CH_2$, $=CH—CH_3$, $=C(CH_3)—CH_3$, $=C(CH_3)—C_2H_5$ or $=C(C_2H_5)—C_2H_5$.

Cycloalkyl is a carbocyclic saturated ring system having preferably 3–8 carbon atoms, is for example cyclopropyl, cyclobutyl, cyclopentyl or cyclohexyl. In the case of substituted cycloalkyl, this includes cyclic systems with substituents, where the substitutents are attached to the cycloalkyl radical via a double bond, for example an alkylidene group such as methylidene. Substituted cycloalkyl also includes polycyclic aliphatic systems, such as, for example, bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, adamantan-1-yl and adamantan-2-yl.

Cycloalkenyl is a carbocyclic non-aromatic, partially unsaturated ring system having preferably 4–8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. For substituted cycloalkenyl, the illustrations for substituted cycloalkyl apply correspondingly.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example, monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic; unless defined otherwise, it preferably contains one or more, in particular 1, 2 or 3, heteroatoms in the heterocyclic ring, preferably selected from the group consisting of N, O and S; it is preferably an aliphatic heterocyclyl radical having 3 to 7 ring atoms or a heteroaromatic radical having 5 or 6 ring atoms. The heterocyclic radical can, for example, be a heteroaromatic radical or ring (heteroaryl), such as, for example, a mono-, bi- or polycyclic aromatic system, in which at least 1 ring contains one or more heteroatoms. It is preferably a heteroaromatic ring having one heteroatom selected from the group consisting of N, O and S, for example pyridyl, pyrrolyl, thienyl or furyl; furthermore, preferably, it is a corresponding heteroaromatic ring having 2 or 3 heteroatoms, for example pyrimidinyl, pyridazinyl, pyrazinyl, triazinyl, thiazolyl, thiadiazolyl, oxazolyl, isoxazolyl, pyrazolyl, imidazolyl and triazolyl. Furthermore preferably, it is a partially or fully hydrogenated heterocyclic radical having one heteroatom selected from the group consisting of N, O and S, for example oxiranyl, oxetanyl, oxolanyl (=tetrahydrofuryl), oxanyl, pyrrolidyl or piperidyl. Furthermore preferably, it is a partially or fully hydrogenated heterocyclic radical having 2 heteroatoms selected from the group consisting of N, O and S, for example piperazinyl, dioxolanyl, oxazolinyl, isoxazolinyl, oxazolidinyl, isoxazolidinyl and morpholinyl.

Possible substituents for a substituted heterocyclic radical are the substituents mentioned further below, and additionally also oxo. The oxo group can also be present at the hetero ring atoms which can exist in different oxidation states, for example at N and S.

Substituted radicals, such as a substituted alkyl, alkenyl, alkynyl, aryl, phenyl, benzyl, heterocyclyl and heteroaryl radical, are, for example, a substituted radical derived from the unsubstituted skeleton, where the substituents are, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl, haloalkyl alkylthioalkyl, alkoxyalkyl, optionally substituted mono- and dialkylaminoalkyl and hydroxyalkyl; the term "substituted radicals", such as substituted alkyl and the like, includes as substituents, in addition to the saturated hydrocarbon-containing radicals mentioned, the corresponding unsaturated aliphatic and aromatic radicals, such as unsubstituted or substituted alkenyl, alkynyl, alkenyloxy, alkynyloxy, phenyl, phenoxy etc. Substituted cyclic radicals having aliphatic moieties in the ring include cyclic systems having substituents which are attached to the ring via a double bond, for example those substituted by an alkylidene group, such as methylidene or ethylidene. Among the radicals with carbon atoms, preference is given to those having 1 to 4 carbon atoms, in particular 1 or 2 carbon atoms. In general, preference is given to substituents selected from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino, such as mono- or disubstituted amino, is a radical from the group of the substituted amino radicals which are N-substituted, for example, by one or two identical or different radicals selected from the group consisting of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having 1 to 4 carbon atoms; aryl is preferably phenyl or substituted phenyl; for acyl, the definition mentioned further below applies, preferably $(C_1-C_4)$-alkanoyl. This applies correspondingly to substituted hydroxylamino or hydrazino.

Unsubstituted or substituted phenyl is preferably phenyl which is unsubstituted or mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyls, 2-, 3- and 4-chlorophenyl, 2-, 3- and 4-fluorophenyl, 2-, 3- and 4-trifluoromethylphenyl, 2,4-, 3,5-, 2,5- and 2,3-dichlorophenyl and difluorophenyl, 2,3, 4-trifluoro- and trichlorophenyl, o-, m- and p-methoxyphenyl.

Acyl is a radical of an organic acid which is formally formed by removing a hydroxyl group from the acid function, where the organic radical in the acid can also be attached to the acid function via a heteroatom. Examples of acyl are the radical —CO—R of a carboxylic acid HO—CO—R and radicals of acids derived therefrom, such as thiocarboxylic acid, unsubstituted or N-substituted iminocarboxylic acids or the radical of carbonic monoesters, N-substituted carbamic acids, sulfonic acids, sulfinic acids, N-substituted sulfonamide acids, phosphonic acids, phosphinic acids.

The active compounds (A) are suitable for weed control in a number of crop plants, for example in economically important crops such as cereals wheat, barley, rice, maize and sorghum, or dicotyledonous crops, such as soya bean, sunflower and sugar cane, (including ®Liberty link corn and ®Round-up Ready corn or soybean). Of particular interest is the use in cereals such as wheat (including durum wheat) and barley, in particular wheat. These crops are likewise preferred for the herbicide-safener combinations (A)+(B).

Preference is given to herbicide-safener combinations comprising one or more compounds (A) and an effective amount of one or more compounds (B) selected from the group consisting of:

(B1.1) compounds of the phenylpyrazolin-3-carboxylic acid type, for example of the formula (I):

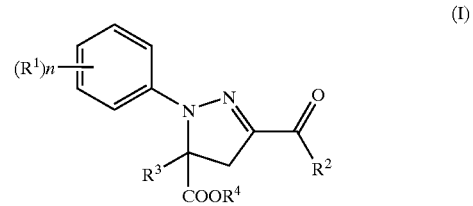

in which $R^1$ are identical or different and are halogen, $(C_1-C_4)$-alkyl, $(C_1-C_4)$-alkoxy, nitro or $(C_1-C_4)$-haloalkyl, n is an integer from 0 to 5, preferably from 0 to 3, $R^2$ is $OR^5$, $SR^6$ or $NR^7R^8$ or a saturated or unsaturated 3- to 7-membered heterocycle having at least one nitrogen atom and up to 3 heteroatoms, preferably selected from the group consisting of O and S, which is attached to the carbonyl group in formula (I) via the nitrogen atom and which is unsubstituted or substituted by radicals selected from the group consisting of $(C_1-C_4)$-alkyl, $(C_1-C_4)$-alkoxy and unsubstituted or substituted phenyl, preferably a radical of the formula $OR^5$; $NHR^7$ or $N(CH_3)_2$, in particular of the formula $OR^5$, $R^3$ is hydrogen, $(C_1-C_8)$-alkyl, $(C_1-C_8)$-haloalkyl, $(C_3-C_{12})$-cycloalkyl or substituted or unsubstituted phenyl, $R^4$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkyl-silyl, $R^5$, $R^6$, $R^7$ independently of one another are hydrogen or an unsubstituted or substituted aliphatic hydrocarbon radical, preferably having a total of 1 to 18 carbon atoms, and $R^8$ is hydrogen, $(C_1-C_6)$-alkyl, $(C_1-C_6)$-alkoxy or substituted or unsubstituted phenyl, preferably compounds such as ethyl 1-(2,4-dichlorophenyl)-5-(ethoxycarbonyl)-5-methyl-2-pyrazoline-3-carboxylate (B1.1.1) ("Mefenpyr-diethyl", see "The Pesticide Manual", 12th edition 2000, pp. 594–595), and related compounds as described in WO 91/07874, ("The Pesticide Manual", 12th edition, is hereinbelow also abbreviated "PM"), (B1.2) derivatives of the phenylpyrazolecarboxylic acid type, for example of the formula (II):

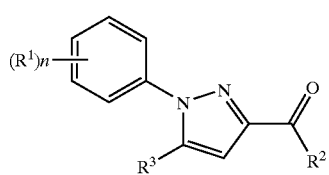

in which
R$^1$, n, R$^2$ and R$^3$ are as defined under formula (I), preferably compounds such as ethyl 1-(2,4-dichlorophenyl)-5-methylpyrazole-3-carboxylate (B1.2.1), ethyl 1-(2,4-dichlorophenyl)-5-isopropylpyrazole-3-carboxylate (B1.2.2), ethyl 1-(2,4-dichlorophenyl)-5-(1,1-dimethylethyl)pyrazole-3-carboxylate (B1.2.3), ethyl 1-(2,4-dichlorophenyl)-5-phenylpyrazole-3-carboxylate (B1.2.4) and related compounds as described in EP-A-333 131 and EP-A-269 806, (B1.3) compounds of the triazolecarboxylic acid type, for example of the formula (III):

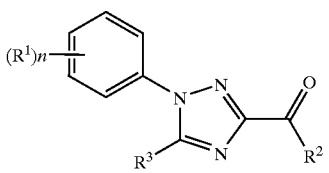

in which
R$^1$, n, R$^2$ and R$^3$ are as defined under formula (I), preferably fenchlorazole(ethyl ester), i.e. ethyl 1-(2,4-dichlorophenyl)-5-trichloromethyl-(1H)-1,2,4-triazole-3-carboxylate (B1.3.1) and related compounds as described in EP-A-174 562 and EP-A-346 620, (B1.4) compounds of the 5-benzyl-, 5-phenyl- or 5,5-diphenyl-2-isoxazoline-3-carboxylic acid type, for example of the formula (IV):

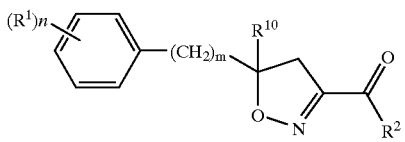

in which
R$^1$, n and R$^2$ are as defined under formula (I) and
R$^{10}$ is hydrogen, (C$_1$–C$_8$)-alkyl, (C$_1$–C$_8$)-haloalkyl, (C$_3$–C$_{12}$)-cycloalkyl or substituted or unsubstituted phenyl and
m is 0 or 1,
preferably compounds such as
ethyl 5-(2,4-dichlorobenzyl)-2-isoxazoline-3-carboxylate (B1.4.1) or ethyl 5-phenyl-2-isoxazoline-3-carboxylate (B1.4.2) and related compounds as described in WO 91/08202, or
ethyl 5,5-diphenyl-2-isoxazolinecarboxylate (B1.4.3) ("isoxadifen-ethyl") or the n-propyl ester (B1.4.4) or
ethyl 5-(4-fluorophenyl)-5-phenyl-2-isoxazoline-3-carboxylate (B1.4.5) as described in WO-A-95/07897, (B1.5) active compounds of the thiazolecarboxylic esters type which are known as seed dressings, such as, for example, "flurazole" (PM, pp. 450–451) (=benzyl 2-chloro-4-trifluoromethyl-1,3-thiazole-5-carboxylate), which is known as a seed-dressing safener for millet against alachlor and metolachlor damage, (B1.6) dimepiperate (="MY-93", PM, pp. 302–303) (=S-1-methyl-1-phenylethyl piperidine-1-thiocarboxylate), which is known as safener for rice against damage by the herbicide molinate, (B2) active compounds which, in addition to a herbicidal action against harmful plants, also have safener action on crop plants such as rice, selected from the group consisting of (B2.1) daimuron (="SK 23", PM, p. 247) (=1-(1-methyl-1-phenylethyl)-3-p-tolylurea), which is known as a safener for rice against damage of the herbicide imazosulfuron, (B2.2) cumyluron (="JC-940", PM, p. 209–210) (=3-(2-chlorophenylmethyl)-1-(1-methyl-1-phenylethyl)urea, see JP-A-60087254), which is known as safener for rice against damage by some herbicides, (B2.3) methoxyphenon (="NK 049"=3,3'-dimethyl-4-methoxybenzophenone), which is known as a safener for rice against damage by some herbicides, (B2.4) CSB (=1-bromo-4-(chloromethylsulfonyl)benzene) (CAS-Reg. No. 54091-06-4 from Kumiai), which is known as safener for rice against damage by some herbicides, (B3.1) N'-acyl-N-benzoyl-aminobenzolsulfonamides of the formula (V) and their salts:

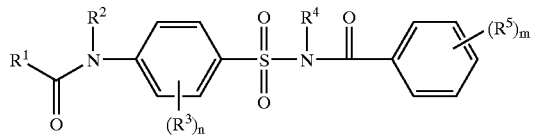

as described in WO-A-97/45016, in which
R$^1$ is hydrogen, a hydrocarbon radical, a hydrocarbon-oxy radical, a hydrocarbon-thio radical or a heterocyclyl radical, which is preferably attached via a carbon atom, where each of the 4 last-mentioned radicals is unsubstituted or substituted by one or more identical or different radicals selected from the group consisting of halogen, cyano, nitro, amino, hydroxyl, carboxyl, formyl, carboxamide, sulfonamide and radicals of the formula Z$^a$-R$^a$, where each hydrocarbon moiety has preferably 1 to 20 carbon atoms and a carbon-containing radical R$^1$, including substituents, has preferably 1 to 30 carbon atoms, R$^2$ is hydrogen or (C$_1$–C$_4$)-alkyl, preferably hydrogen, or
R$^1$ and R$^2$ together with the group of the formula —CO—N— are the radical of a 3- to 8-membered saturated or unsaturated ring, R$^3$ are identical or different and are halogen, cyano, nitro, amino, hydroxyl, carboxyl, formyl, CONH$_2$, SO$_2$NH$_2$ or a radical of the formula Z$^b$-R$^b$, R$^4$ is hydrogen or (C$_1$–C$_4$)-alkyl, preferably hydrogen, R$^5$ are identical or different and are halogen, cyano, nitro, amino, hydroxyl, carboxyl, CHO, CONH$_2$, SO$_2$NH$_2$ or a radical of the formula Z$^c$-R$^c$, R$^a$ is a hydrocarbon radical or a heterocyclyl radical, where each of the two last-mentioned radicals is unsubstituted or substituted by one or more identical or different radicals selected from the group consisting of halogen, cyano, nitro, amino, hydroxyl, mono- and di-[($C_1$–$C_4$)-alkyl]amino, or an alkyl radical in which a plurality, preferably 2 or 3, of non-adjacent $CH_2$ groups are in each case replaced by an oxygen atom, $R^b$, $R^c$ are identical or different and are a hydrocarbon radical or a heterocyclyl radical, where each of the two last-mentioned radicals is unsubstituted or substituted by one or more identical or different radicals selected from the group consisting of halogen, cyano, nitro, amino, hydroxyl, phosphoryl, halo-($C_1$–$C_4$)-alkoxy, mono- and di-[($C_1$–$C_4$)-alkyl]amino, or an alkyl radical in which a plurality, preferably 2 or 3, of non-adjacent $CH_2$ groups are in each replaced by an oxygen atom, $Z^a$ is a divalent group of the formula O, S, CO, CS, CO—O, CO—S, O—CO, S—CO, SO, $SO_2$, NR*, CO—NR*, NR*—CO, $SO_2$—NR* or NR*—$SO_2$, where the bond indicated on the right-hand side of the divalent group in question is the bond to the radical $R^a$ and where the radicals R* in the 5 last-mentioned radicals independently of one another are in each case H, ($C_1$–$C_4$)-alkyl or halo-($C_1$–$C_4$)-alkyl, $Z^b$, $Z^c$ independently of one another are a direct bond or a divalent group of the formula O, S, CO, CS, CO—O, CO—S, O—CO, S—CO, SO, $SO_2$, NR*, $SO_2$—NR*, NR*—$SO_2$, CO—NR* or NR*—CO, where in the case of assymetrical divalent groups the atom located on the right-hand side is attached to the radical $R^b$ or $R^c$, and where the radicals R* in the 5 last-mentioned radicals independently of one another are in each case H, ($C_1$–$C_4$)-alkyl or halo-($C_1$–$C_4$)-alkyl, n is an integer from 0 to 4, preferably 0, 1 or 2, in particular 0 or 1, and m is an integer from 0 to 5, preferably 0, 1, 2 or 3, in particular 0, 1 or 2, for example the compound 1-(4-(N-2-methoxybenzoylsulfamoyl)phenyl)-3-methylurea, i.e. formula (V) in which R1=$CH_3NH$—, $R^2$=H, n=0, $R^4$=H and $(R^5)_m$=2-methoxy (B3.1.1), (B3.2) acylsulfamoylbenzamides of the formula (VI), if appropriate also in salt form,

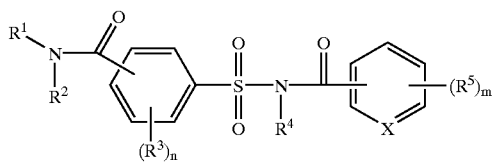

(VI)

as described in the International Application No. PCT/EP98/06097 (WO-A-99/16744), in which X is CH or N, $R^1$ is hydrogen, heterocyclyl or a hydrocarbon radical, where the two last-mentioned radicals are unsubstituted or substituted by one or more identical or different radicals selected from the group consisting of halogen, cyano, nitro, amino, hydroxyl, carboxyl, CHO, $CONH_2$, $SO_2NH_2$ and $Z^d$-$R^d$, $R^2$ is hydrogen, hydroxyl, ($C_1$–$C_6$)-alkyl, ($C_2$–$C_6$)-alkenyl, ($C_2$–$C_6$)-alkynyl, ($C_1$–$C_6$)-alkoxy, ($C_2$–$C_6$)-alkenyloxy, where the five last-mentioned radicals are unsubstituted or substituted by one or more identical or different radicals selected from the group consisting of halogen, hydroxyl, ($C_1$–$C_4$)-alkyl, ($C_1$–$C_4$)-alkoxy and ($C_1$–$C_4$)-alkylthio, or $R^1$ and $R^2$ together with the nitrogen atom that carries them are a 3- to 8-membered saturated or unsaturated ring, $R^3$ are identical or different and are halogen, cyano, nitro, amino, hydroxyl, carboxyl, CHO, $CONH_2$, $SO_2NH_2$ or $Z^e$-$R^e$, $R^4$ is hydrogen, ($C_1$–$C_4$)-alkyl, ($C_2$–$C_4$)-alkenyl or ($C_2$–$C_4$)-alkynyl, $R^5$ are identical or different and are halogen, cyano, nitro, amino, hydroxyl, carboxyl, phosphoryl, CHO, $CONH_2$, $SO_2NH_2$ or $Z^f$-$R^f$, $R^d$ is a ($C_2$–$C_{20}$)-alkyl radical whose carbon chain is interrupted once or a plurality of times by oxygen atoms, is heterocyclyl or a hydrocarbon radical, where the two last-mentioned radicals are unsubstituted or substituted by one or more identical or different radicals selected from the group consisting of halogen, cyano, nitro, amino, hydroxy, mono- and di-[($C_1$–$C_4$)-alkyl]amino;

$R^e$, $R^f$ are identical or different and are a ($C_2$–$C_{20}$)-alkyl radical whose carbon chain is interrupted once or a plurality of times by oxgen atoms, or are heterocyclyl or a hydrocarbon radical, where the two last-mentioned radicals are unsubstituted or substituted by one or more identical or different radicals selected from the group consisting of halogen, cyano, nitro, amino, hydroxyl, phosphoryl, ($C_1$–$C_4$)-haloalkoxy, mono- and di-[($C_1$–$C_4$)-alkyl]amino, $Z^d$ is a divalent unit selected from the group consisting of O, S, CO, CS, C(O)O, C(O)S, SO, $SO_2$, NR*, C(O)NR* or $SO_2NR^*$, $Z^e$, $Z^f$ are identical or different and are a direct bond or a divalent unit selected from the group consisting of O, S, CO, CS, C(O)O, C(O)S, SO, $SO_2$, NR*, $SO_2NR^*$ or C(O)NR*, R* is hydrogen, ($C_1$–$C_4$)-alkyl or ($C_1$–$C_4$)-haloalkyl, n is an integer from 0 to 4, and m is, in the case that X is CH, an integer from 0 to 5 and, in the case that X is N, an integer from 0 to 4, for example the compound 4-(2-methoxybenzoylsulfamoyl)-N-cyclopropylbenzamide (B3.2.1), and including the stereoisomers and the agriculturally useful salts thereof.

Among the safeners mentioned, those of group (B1.1) are preferred. Also preferred are the safeners (B1.1.1) and (B1.2.1) to (B1.2.4), (B1.3.1), (B1.4.1) to (B1.4.5), (B2.1.) to (B2.4), (B3.1.1) and (B3.2.1). Of special interest are (B1.1.1) and (B1.4.3), in particular (B1.1.1).

Preferred combinations include or are:

(A)+(B1.1), (A)+(B1.2), (A)+(B1.3), (A)+(B1.4), (A)+(B1.5), (A)+(B1.6), (A)+(B2.1), (A)+(B2.2), (A)+(B2.3), (A)+(B2.4), (A)+(B3.1) or (A)+(B3.2), with the exception of combinations comprising (A1)+(B1.4).

Further preferred combinations include or are:

(A1)+(B1.1), (A1)+(B1.2), (A1)+(B1.3), (A1)+(B1.5), (A1)+(B1.6), (A1)+(B2.1) (A1)+(B2.2), (A1)+(B2.3), (A1)+(B2.4), (A1)+(B3.1) or (A1)+(B3.2).

More preferred combinations include or are:

(A)+(B1.1.1), (A)+(B1.2.1), (A)+(B1.2.2), (A)+(B1.2.3), (A)+(B1.2.4), (A)+(B1.3.1), (A)+(B1.4.1), (A)+(B1.4.2), (A)+(B1.4.3), (A)+(B1.4.4), (A)+(B1.4.5), (A)+(B2.1), (A)+(B2.1), (A)+(B2.2), (A)+(B2.3), (A)+(B2.4), (A)+

(B3.1.1), (A)+(B3.2.1), with the exception of combinations comprising (A1)+(B1.4.1), (A)+(B1.4.2), (A)+(B1.4.3), (A)+(B1.4.4) or (A)+(B1.4.5).

Particularly preferred combinations include or are:
(A1)+(B1.1.1), (A1)+(B1.2.1), (A1)+(B1.2.2), (A1)+(B1.2.3), (A1)+(B1.2.4), (A1)+(B1.3.1), (A1)+(B2.1), (A1)+(B2.2), (A1)+(B2.3), (A1)+(B2.4), (A1)+(B3.1.1), and (A1)+(B3.2.1).

The combinations of the compounds (A) or their salts and the safeners (B) can be used, for example, as such or in the form of their preparations (formulations) combined with other pesticidally active substances, such as, for example, insecticides, acaricides, nematicides, herbicides, fungicides, safeners, fertilizers and/or growth regulators, for example in the form of a finished formulation or tank mixes. The preferred additional active compounds are herbicides.

Also preferred according to the invention are those combinations in which one or more further active compounds of a different structure [active compounds (C)] are added, such as:
(A)+(B1)+(C), (A)+(B2)+(C) or (A)+(B3)+(C), wherein (C) is one or more other active compounds, with the exception of combinations comprising (A1)+(B1.4).

Preferred combinations in which one or more further active compounds of a different structure [active compounds (C)] are added include or are:
(A1)+(B1)+(C), (A1)+(B2)+(C) or (A1)+(B3)+(C), with the exception of combinations comprising (A1)+(B1.4).

Further preferred combinations in which one or more further active compounds of a different structure [active compounds (C)] are added include or are:
(A)+(B1.1)+(C), (A)+(B1.2)+(C), (A)+(B1.3)+(C), (A)+(B1.4)+(C), (A)+(B1.5)+(C), (A)+(B1.6)+(C), (A)+(B2.1)+(C), (A)+(B2.2)+(C), (A)+(B2.3)+(C), (A)+(B2.4)+(C), (A)+(B3.1)+(C) or (A)+(B3.2)+(C), with the exception of combinations comprising (A1)+(B1.4).

More preferred combinations in which one or more further active compounds of a different structure [active compounds (C)] are added include or are:
(A1)+(B1.1)+(C), (A1)+(B1.2)+(C), (A1)+(B1.3)+(C), (A1)+(B1.5)+(C), (A1)+(B1.6)+(C), (A1)+(B1.7)+(C), (A1)+(B2.1)+(C), (A1)+(B2.2)+(C), (A1)+(B2.3)+(C), (A1)+(B2.4)+(C), (A1)+(B3.1)+(C) or (A1)+(B3.2)+(C).

Most preferred combinations are (A1)+(B1.1.1)+(C).

Suitable active compounds (C) which can be combined with the active compounds according to the invention in mixed formulations or in a tank mix are, for example, known active compounds, preferably herbicides, as described, for example, in Weed Research 26, 441–445 (1986), or "The Pesticide Manual", 12th edition, The British Crop Protection Council and the Royal Soc. of Chemistry, 1997 and the literature cited therein. For example, the following active compounds may be mentioned as known herbicides or plant growth regulators and which can be combined with the compounds of the formula (I); hereinbelow, the compounds are either named by the "common name" (in most cases in English spelling) in accordance with the International Organization for Standardization (ISO) or by the chemical names, if appropriate together with a customary code number:

acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; amitrol; AMS, i.e. ammonium sulfamate; anilofos; asulam; atrazin; azafenidin, azimsulfurone (DPX-A8947); aziprotryn; barban; BAS 516 H, i.e. 5-fluoro-2-phenyl-4H-3,1-benzoxazin-4-one; beflubutamid, benazolin(-ethyl); benfluralin; benfuresate; bensulfuron(-methyl); bensulide; bentazone; benzobicyclon, benzofenap; benzofluor; benzoylprop(-ethyl); benzthiazuron; bialaphos; bifenox; bispyribac(-sodium), bromacil; bromobutide; bromofenoxim; bromoxynil; bromuron; buminafos; busoxinone; butachlor; butafenacil, butamifos; butenachlor; buthidazole; butralin; butroxydim, butylate; cafenstrole (CH-900); carbetamide; carfentrazone(-ethyl) (ICI-A0051); caloxydim, CDAA, i.e. 2-chloro-N,N-di-2-propenylacetamide; CDEC, i.e. 2-chloroallyl diethyldithiocarbamate; chlomethoxyfen; chlorazifop-butyl, chlormesulon (ICI-A0051); chlorbromuron; chlorbufam; chlorfenac; chlorflurecol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon(-methyl and -ethyl), cinmethylin; cinosulfuron; clefoxydim, clethodim; clodinafop and its ester derivatives (for example clodinafop-propargyl); clomazone; clomeprop; cloproxydim; clopyralid; clopyrasulfuron(-methyl), cloransulam(-methyl), cumyluron (JC 940); cyanazine; cycloate; cyclosulfamuron (AC 104); cycloxydim; cycluron; cyhalofop and its ester derivatives (for example the butyl ester, DEH-1 12); cyperquat; cyprazine; cyprazole; daimuron; 2,4-D, 2,4-DB; 2,4-DB, dalapon; desmedipham; desmetryn; di-allate; dichlobenil; dichlorprop; diclofop and its esters such as diclofop-methyl; diclosulam, diethatyl(-ethyl); difenoxuron; difenzoquat; diflufenican; diflufenzopyr, dimefuron; dimepiperate, dimethachlor; dimethametryn-; dimethenamid (SAN-582H); dimethazone, dimexyflam, dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example the ethyl ester, HN-252); ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]phenyl]ethanesulfonamide; fenoprop; fenoxan, fenoxaprop and fenoxaprop-P and their esters, for example fenoxaprop-P-ethyl and fenoxaprop-ethyl; fenoxydim; fentrazamide, fenuron; flamprop(-methyl or -isopropyl or -isopropyl-L); flazasulfuron; floazulate, florasulam, fluazifop and fluazifop-P and their esters, for example fluazifop-butyl and fluazifop-P-butyl; flucarbazone(-sodium), fluchloralin; flumetsulam; flumeturon; flumiclorac(-pentyl), flumioxazin (S-482); flumipropyn; fluometuron, fluorochloridone, fluorodifen; fluoroglycofen(-ethyl); flupoxam (KNW-739); flupropacil (UBIC-4243); flupyrsulfuron(-methyl or -sodium), flurenol(-butyl), fluridone; flurochloridone; fluroxypyr(-meptyl); flurprimidol, flurtamone; fluthiacet(-methyl), fluthiamide, fomesafen; foramsulfuron, fosamine; furyloxyfen; glufosinate(-ammonium); glyphosate(-isopropylammonium); halosafen; halosulfuron(-methyl) and its esters (for example the methyl ester, NC-319); haloxyfop and its esters; haloxyfop-P (=R-haloxyfop) and its esters; hexazinone; imazamethabenz(-methyl); imazapyr; imazaquin and salts such as the ammonium salt; imazamethapyr, imazamox, imazapic, imazethamethapyr; imazethapyr; imazosulfuron; indanofan, iodosulfuron(-methyl-sodium), ioxynil; isocarbamid; isopropalin; isoproturon; isouron; isoxaben; isoxachlortole, isoxaflutole, isoxapyrifop; karbutilate; lactofen; lenacil; linuron; MCPA; MCPB; mecoprop; mefenacet; mefluidid; mesosulfuron, mesotrione, metamitron; metazachlor; methabenzthiazuron; metham; methazole; methoxyphenone; methyldymron; metabenzuron, methobenzuron; metobromuron; (alpha-)metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2, 4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron, oxaziclomefone, oxyfluorfen; paraquat; pebulate; pelargonic acid, pendimethalin, pentoxazone, perfluidone; phenisopham; phenmedipham; picloram; picolinafen, piperophos; piributicarb; pirifenop-butyl; pretilachlor; primisulfuron(-methyl); procarbazone-(sodium), procyazine; prodiamine; profluralin; proglinazine(-ethyl); prometon; prometryn; propachlor; propanil; propaquizafop and its esters; propazine; propham; propisochlor; propyzamide; prosulfalin; prosulfocarb; prosulfuron (CGA-152005); prynachlor; pyraflufen(-ethyl), pyrazolinate; pyrazon; pyrazosulfuron(-ethyl); pyrazoxyfen; pyribenzoxim, pyributicarb, pyridafol, pyridate; pyrimidobac(-methyl), pyrithiobac(-sodium) (KIH-2031); pyroxofop and its esters (for example the propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl) phenoxy]-2-naphthalenyl]oxy]propanoic acid and its methyl ester; sulcotrione, sulfentrazon (FMC-97285, F-6285); sulfazuron; sulfometuron(-methyl); sulfosate (ICI-A0224); sulfosulfuron, TCA; tebutam (GCP-5544); tebuthiuron; tepraloxydim, terbacil; terbucarb; terbuchlor; terbumeton; terbuthylazine; terbutryn; TFH 450, i.e. N,N-diethyl-3-[(2-ethyl-6-methylphenyl)-sulfonyl]-1H-1,2,4-triazole-1-carboxamide; thenylchlor (NSK-850); thiafluamide, thiazafluron; thiazopyr (Mon-13200); thidiazimin (SN-24085); thifensulfuron(-methyl); thiobencarb; tiocarbazil; tralkoxydim; tri-allate; triasulfuron; triaziflam, triazofenamide; tribenuron(-methyl); triclopyr; tridiphane; trietazine; trifluralin; triflusulfuron and its esters (for example the methyl ester, DPX-66037); trimeturon; tritosulfuron, tsitodef; vernolate; WL 110547, i.e. 5-phenoxy-1-[3-(trifluoromethyl)pheny]-1H-tetrazole; BAY MKH 6561, UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For combinations of the last-mentioned type with three or more active compounds, the preferred conditions illustrated below in particular for herbicide-safener combinations according to the invention primarily also apply if the combinations comprise the two-compound combinations according to the invention.

In individual cases, it may be advantageous to combine one of the compounds (A) with a plurality of compounds (B).

The application rate of the herbicides (A) can be varied within wide limits, the optimum amount depending on the herbicide in question, the spectrum of harmful plants and the crop plants. In general, the application rate is in the range from 0.001 g to 12 kg, preferably 10 g to 3 kg, very particularly 20 g to 2 kg of active compound (a.i.) per ha.

The herbicidally active compounds and the safeners can be applied together (as finished formulation or by the tank-mix method) or sequentially in any order. The weight ratio herbicide (A) : safener (B) can vary within wide limits and is, for example, in the range from 1:200 to 200:1, preferably from 1:100 to 100:1, in particular from 1:20 to 20:1, most preferably from 1:10 to 10:1. The amounts of herbicidally active compound and safener which are optimal in each case depend on the active compound (A) and the safener (B) in question and on the type of crops to be treated, and they can be determined in each case by appropriate preliminary experiments. Depending on their properties, the safeners may be used for pre-treating the seed of the crop plant (seed dressing) or the seedlings or be incorporated into the seed furrow prior to sowing. In the pretreatment of seedlings it is possible, for example, to spray the roots or the entire seedling with a solution of the safener or to dip them into such a solution. The use of one or more herbicides can then be carried out by the pre-emergence or post-emergence method.

Alternatively, it is possible to apply the safeners together with the herbicides, before or after emergence of the plants. Pre-emergence treatment includes both the treatment of the area under cultivation prior to sowing and the treatment of the areas under cultivation where the crops have been sown but not yet emerged. A sequential procedure, where the treatment with safener is carried out first followed, preferably closely, by application of the herbicide, is also possible. In individual cases, it may also be expedient to apply the safener after application of the herbicide.

In general, simultaneous application of safener and herbicide in the form of tank mixes or finish formulations is preferred.

The amount of safener used varies according to a number of parameters including the particular safener employed, the crop to be protected, the amount and rate of herbicide applied, the soil type and climatic conditions prevailing. Also, the selection of the specific safener for use in the method of the invention, the manner in which it is to be applied and the determination of the activity which is non-phytotoxic but antidotally effective, can be readily performed in accordance with common practice in the art. The application rate of safener can vary within wide limits and is generally in the range from 0.001 to 5 kg, preferably from 0.005 to 0.5 kg, of safener (a.i.) per hectare, or for seed treatment use is, for example, from 0.01 g to 10 g a.i. safener per kg seed, preferably 0.05 g to 1 g a.i. safener per kg seed, in particular 0.1 g to 0.5 g a.i. safener per kg seed.

If solutions of safeners are used in the seed treatment method wherein the seeds are soaked in the safener solution, the concentration of the safener in the solution is for example from 1 to 10000 ppm, preferably 100 to 1000 ppm based on weight.

Accordingly, the invention also provides a method for protecting crop plants against phytotoxic side effects of a herbicide (A), which method comprises the application of an amount, acting as an antidote, of one or more safeners (B) before, after or simultaneously with the herbicide (A) to the plants, parts of plants, plant seeds or the area under cultivation.

The herbicide-safener combinations according to the invention (i.e. the herbicidal compositions) have excellent herbicidal activity against a broad spectrum of economically important mono- and dicotyledonous harmful plants. The combinations also act efficiently on perennial weeds which produce shoots from rhizomes, root stocks or other perennial organs and which are difficult to control. The herbicidal effects of the combinations are similar to those of the herbicides (A) when used alone at comparable application rates.

If the combinations according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the combinations are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Owing to their herbicidal and plant growth-regulatory properties, the combinations can be employed for controlling harmful plants in known crops or in still to be developed genetically engineered plants. Transgenic plants generally have particularly advantageous properties, for example resistance to certain pesticides, above all certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested product are known.

The combinations according to the invention are preferably employed in economically important transgenic crops of useful and ornamental plants, for example of cereals such as wheat, barley, rye, oats, millett, rice, manioc and maize or else in crops of sugar-beet, cotton, soya bean, oil seed rape, potatoes, tomatoes, peas and other vegetable species.

The invention also provides the use of the herbicidal compositions comprising combinations of (A)+(B) for controlling harmful plants, preferably in plant crops.

The active compound combinations according to the invention can be present both as mixed formulations of the two components, if appropriate with other active compounds, additives and/or customary formulation auxiliaries, which are then applied in a customary manner diluted with water, or be prepared as so-called tank mixes by joint dilution of the separately formulated or partially separately formulated components with water.

The compounds (A) and (B) or their combinations can be formulated in various ways depending on the prevailing biological and/or chemico-physical parameters. Examples of suitable formulation options are: wettable powders (WP), emulsifiable concentrates (EC), aqueous solutions (SL), emulsions (EW), such as oil-in-water and water-in-oil emulsions, sprayable solutions or emulsions, oil- or water-based dispersions, suspoemulsions, dusts (DP), seed-dressing compositions, granules for broadcasting and soil application, or water-dispersible granules (WG), ULV formulations, micro-capsules or waxes.

The individual formulation types are known in principle and are described, for example, in Winnacker-Küchler, "Chemische Technologie" [Chemical Technology], Volume 7, C. Hauser Verlag Munich, 4th. Edition 41986; van Valkenburg, "Pesticides Formulations", Marcel Dekker, N.Y., 1973; K. Martens, "Spray Drying Handbook", 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschoft, Stuttgart 1976; Winnacker-Küchler, "Chemische Technologie" [Chemical Technology], Volume 7, C. Hauser Verlag Munich, 4th Edition 1986.

Based on these formulations it is also possible to produce combinations with other pesticidally active substances, such as other herbicides, fungicides or insecticides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic or nonionic type (wetting agents, dispersants), for example polyethoxylated alkyl phenols, polyethoxylated fatty alcohols, polyethoxylated fatty amines, alkanesulfonates, alkylbenzenesulfonates, sodium ligninsulfonate, sodium 2,2'-dinaphthylmethane-6,6'-disulfonate, sodium dibutyinaphthalene-sulfonate or else sodium oleoylmethyltaurinate.

Emulsifiable concentrates are prepared by dissolving the active compound in an organic solvent, for example butanol, cyclohexanone, dimethylformamide, xylene or else relatively high-boiling aromatic compounds or hydrocarbons with the addition of one or more surfactants of ionic or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylene sorbitan esters.

Dusts are obtained by grinding the active compound with finely divided solid substances, for example talc, natural clays, such as kaolin, bentonite and pyrophyllite, or diatomaceous earth.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by processes such as spray-drying, fluidized-bed granulation, disk granulation, mixing using high-speed mixers, and extrusion without solid inert material.

The agrochemical formulations generally contain from 0.1 to 99% by weight, in particular from 2 to 95% by weight, of active compounds of types A and/or B, the following concentrations being customary, depending on the type of formulations: In wettable powders the concentration of active compound is, for example, from about 10 to 95% by weight, the remainder to 100% by weight consisting of customary formulation constituents. In emulsifiable concentrates the concentration of active compound can be, for example, from 5 to 80% by weight.

Formulations in the form of dusts usually contain from 5 to 20% by weight of active compound, while sprayable solutions contain from about 0.2 to 25% by weight of active compound.

In the case of granules, such as dispersible granules, the content of active compound depends partly on whether the active compound is in liquid or solid form and on which granulation auxiliaries and fillers that are used. In water-dispersible granules the content is generally between 10 and 90% by weight.

In addition, said formulations of active compound may comprise the tackifiers, wetting agents, dispersants, emulsifiers, preservatives, antifreeze agents and solvents, fillers, colorants and carriers, antifoams, evaporation inhibitors, pH and viscosity regulators, thickeners and/or fertilizers which are customary in each case.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions are conventionally not diluted any further with other inert substances prior to use.

The herbicidal compounds can be applied to the plants, parts of the plants, seeds of the plants or the area under cultivation (tilled soil), preferably to the green plants and parts of the plants and, if desired, additionally to the tilled soil.

A possible use is the joint application of the active compounds in the form of tank mixes, where the concentrated formulations of the individual active substances, in the form of their optimal formulations, are mixed jointly with water in the tank, and the resulting spray mixture is applied.

A joint herbicidal formulation of the combination according to the invention of the active compounds (A) and (B) has the advantage that it can be applied more easily because the amounts of the components have already been adjusted to one another in the correct ratio. Moreover, the auxiliaries of the formulation can be selected to suit each other in the best possible way, while a tank mix of various formulations may result in undesirable combinations of auxiliaries.

A. GENERAL FORMULATION EXAMPLES a) A dust is obtained by mixing 10 parts by weight of an active compound/active compound mixture and 90 parts by weight of talc as inert substance and comminuting the mixture in a hammer mill.

b) A wettable powder which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of ethoxylated nonylphenol as emulsifier.

e) Water-dispersible granules are obtained by mixing 75 parts by weight of an active compound/active compound mixture, 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill and granulating the powder in a fluidized bed by spraying on water as granulation liquid.

f) Water-dispersible granules are also obtained by homogenizing and precomminuting, in a colloid mill, 25 parts by weight of an active compound/active compound mixture, 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance nozzle.

B. BIOLOGICAL EXAMPLES

The following non-limiting Example illustrates the invention.

1. Post-Emergence Effect on Weeds and Crop Plant Selectivity (Field Trials)

Crop plants were grown outdoors on plots under natural outdoor conditions, and seeds or rhizome pieces of typical harmful plants were laid out or the natural weed growth was utilized. Treatment with the compositions according to the invention was carried out after the harmful plants had emerged and the crop plants were at the growth stage stated below. After the application, the effect of the composition was scored visually by comparison with untreated controls.

Table 1 shows typical results obtained by post-emergence application of a mixture of the dicamba salt (140 g a.i./ha) and mefenpyr-diethyl (50 g a.i./ha) to wheat at the 3-tiller growth stage, compared to the effect of the dicamba salt alone. Each figure refers to the average of three trial results. Assessment 39 days after treatment showed that a good safening effect was obtained in wheat. No difference in the weed control, including typical cereal weed species, was found as compared to that of dicamba alone.

Abbreviations used in Table 1 below:

| | |
|---|---|
| TRZAS = | Triticum aestivum (wheat) |
| (A1) = | dicamba dimethylammonium salt |
| (B1.1.1) = | mefenpyr-diethyl |

The numbers in the columns refer to the percentage damage to the wheat.

TABLE 1

| Compound No. | Application rate (g ai/ha) | Phytotox (%) on TRZAS |
|---|---|---|
| (A1) | 140 | 27 |
| | 210 | 25 |
| | 280 | 27 |
| (B1.1.1) | 50 | 0 |
| | 120 | 0 |
| (A1) + (B1.1.1) | 140 + 50 | 4 |
| | 210 + 120 | 3 |
| | 280 + 50 | 8 |

What is claimed is:

1. A herbicide-safener combination, which comprises:
   (A) one or more herbicidal auxin type aromatic carboxylic acids or agriculturally acceptable salts thereof, and
   (B) one or more safeners selected from the group consisting of:
      (B1.1) compounds of the phenylpyrazolin-3-carboxylic acid type, and
      (B3.2) acylsulfamoylbenzamides or salts thereof.

2. A herbicide-safener combination as claimed in claim 1 in which component (A) is selected from the group consisting of:
   (A1) 3,6-dichloro-2-methoxybenzoic acid (dicamba) or its salts,
   (A2) 3-amino-2,5-dichlorobenzoic acid (chloramben) or its salts, and
   (A3) 2,3,6-trichlorobenzoic acid (2,3,6-TBA) or its salts.

3. A herbicide-safener combination as claimed in claim 1 in which component (A) is: (A1) 3,6-dichloro-2-methoxybenzoic acid (dicamba) or its salts.

4. A herbicide-safener combination as claimed in claim 1 which comprises as component (B), one or more safeners selected from the group consisting of
   (B1.1) compounds of the phenylpyrazolin-3-carboxylic acid type of the formula (I):

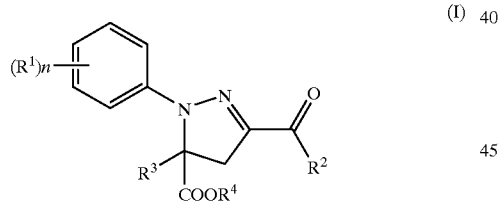

(I)

in which
R$^1$ are identical or different and are halogen, (C$_1$–C$_4$)-alkyl, (C$_1$–C$_4$)-alkoxy, nitro or (C$_1$–C$_4$)-haloalkyl,
n is an integer from 0 to 5,
R$^2$ is OR$^5$, SR$^6$ or NR$^7$R$^8$ or a saturated or unsaturated 3- to 7-membered heterocycle having at least one nitrogen atom and up to 3 heteroatoms, which is attached to the carbonyl group in formula (I) via the nitrogen atom and which is unsubstituted or substituted by radicals selected from the group consisting of (C$_1$–C$_4$)-alkyl, (C$_1$–C$_4$)-alkoxy and unsubstituted or substituted phenyl,
R$^3$ is hydrogen, (C$_1$–C$_8$)-alkyl, (C$_1$–C$_8$)-haloalkyl, (C$_3$–C$_{12}$)-cycloalkyl or substituted or unsubstituted phenyl and
R$^4$ is hydrogen, (C$_1$–C$_8$)-alkyl, (C$_1$–C$_8$)-haloalkyl, (C$_1$–C$_4$)-alkoxy-(C$_1$–C$_4$)-alkyl, (C$_1$–C$_6$)-hydroxyalkyl, (C$_3$–C$_{12}$)-cycloalkyl or tri-(C$_1$–C$_4$)-alkyl-silyl, and R$^5$, R$^6$, R$^7$ independently of one another are hydrogen or an unsubstituted or substituted aliphatic hydrocarbon radical, and
R$^8$ is hydrogen, (C$_1$–C$_6$)-alkyl, (C$_1$–C$_6$)-alkoxy or substituted or unsubstituted phenyl, and
(B3.2) acylsulfamoylbenzamides of the formula (VI), if appropriate also in salt form,

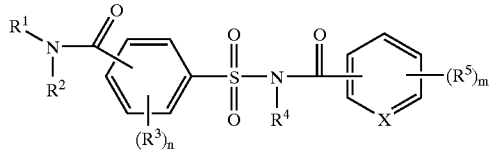

(VI)

in which
X is CH or N,
R$^1$ is hydrogen, heterocyclyl or a hydrocarbon radical, where the two last-mentioned radicals are unsubstituted or substituted by one or more identical or different radicals selected from the group consisting of halogen, cyano, nitro, amino, hydroxyl, carboxyl, CHO, CONH$_2$, SO$_2$NH$_2$ and Z$^d$-R$^d$,
R$^2$ is hydrogen, hydroxyl, (C$_1$–C$_6$)-alkyl, (C$_2$–C$_6$)-alkenyl, (C$_2$–C$_6$)-alkynyl, (C$_1$–C$_6$)-alkoxy, (C$_2$–C$_6$)-alkenyloxy, where the five last-mentioned radicals are unsubstituted or substituted by one or more identical or different radicals selected from the group consisting of halogen, hydroxyl, (C$_1$–C$_4$)-alkyl, (C$_1$–C$_4$)-alkoxy and (C$_1$–C$_4$)-alkylthio, or
R$^1$ and R$^2$ together with the nitrogen atom that carries them are a 3- to 8-membered saturated or unsaturated ring,
R$^3$ are identical or different and are halogen, cyano, nitro, amino, hydroxyl, carboxyl, CHO, CONH$_2$, SO$_2$NH$_2$ or Z$^e$-R$^e$,
R$^4$ is hydrogen, (C$_1$–C$_4$)-alkyl, (C$_2$–C$_4$)-alkenyl or (C$_2$–C$_4$)-alkynyl,
R$^5$ are identical or different and are halogen, cyano, nitro, amino, hydroxyl, carboxyl, phosphoryl, CHO, CONH$_2$, SO$_2$NH$_2$ or Z$^f$-R$^f$,
R$^d$ is a (C$_2$–C$_{20}$)-alkyl radical whose carbon chain is interrupted once or a plurality of times by oxygen atoms, is heterocyclyl or a hydrocarbon radical, where the two last-mentioned radicals are unsubstituted or substituted by one or more identical or different radicals selected from the group consisting of halogen, cyano, nitro, amino, hydroxy, mono- and di-[(C$_1$–C$_4$)-alkyl]amino;
R$^e$, R$^f$ are identical or different and are a (C$_2$–C$_{20}$)-alkyl radical whose carbon chain is interrupted once or a plurality of times by oxgen atoms, or are heterocyclyl or a hydrocarbon radical, where the two last-mentioned radicals are unsubstituted or substituted by one or more identical or different radicals selected from the group consisting of halogen, cyano, nitro, amino, hydroxyl, phosphoryl, (C$_1$–C$_4$)-haloalkoxy, mono- and di-[(C$_1$–C$_4$)-alkyl]amino,
Z$^d$ is a divalent unit selected from the group consisting of O, S, CO, CS, C(O)O, C(O)S, SO, SO$_2$, NR*, C(O)NR* and SO$_2$NR*,
Z$^e$, Z$^f$ are identical or different and are a direct bond or a divalent unit selected from the group consisting of O, S, CO, CS, C(O)O, C(O)S, SO, SO$_2$, NR*, SO$_2$NR* and C(O)NR*,
R* is hydrogen, (C$_1$–C$_4$)-alkyl or (C$_1$–C$_4$)-haloalkyl, n is an integer from 0 to 4, and
m is, in the case that X is CH, an integer from 0 to 5 and, in the case that X is N, an integer from 0 to 4.

5. A herbicide-safener combination as claimed in claim 1, which comprises as component (B), one or more safeners selected from the group consisting of:
ethyl 1-(2,4-dichlorophenyl)-5-(ethoxycarbonyl)-5-methyl-2-pyrazoline-3-carboxylate (B1.1.1) ("Mefenpyr-diethyl"), and 4-(2-methoxybenzoylsulfamoyl)-N-cyclopropylbenzamide (B3.2.1), and the stereoisomers and the agriculturally useful salts thereof.

6. A herbicide-safener combination as claimed in claim 1, which comprises as component (B):
ethyl 1-(2,4-dichlorophenyl)-5-(ethoxycarbonyl)-5-methyl-2-pyrazoline-3-carboxylate (B1.1.1) (mefenpyr-diethyl).

7. A herbicide-safener combination as claimed in claim 1, which comprises the active compounds (A) and (B) in a weight ratio of from 200:1 to 1:200.

8. A herbicide-safener combination as claimed in claim 1, which comprises the active compounds (A) and (B) in a weight ratio of from 100:1 to 1:100.

9. A herbicidal-safener combination as defined in claim 1 which additionally contains formulation auxiliaries.

10. A herbicide-safener combination as claimed in claim 2, which comprises as component (B) ethyl 1-(2,4-dichlorophenyl)-5-(ethoxycarbonyl)-5-methyl-2-pyrazoline-3-carboxylate (B1.1.1) (mefenpyr-diethyl).

11. A herbicide-safener combination as claimed in claim 3, which comprises as component (B) ethyl 1-(2,4-dichlorophenyl)-5-(ethoxycarbonyl)-5-methyl-2-pyrazoline-3-carboxylate (B1.1.1) (mefenpyr-diethyl).

12. A herbicide-safener combination as claimed in claim 11 which comprises active compounds (A) and (B) in a weight ratio of from 200:1 to 1:200.

13. A herbicide-safener combination as claimed in claim 11 which comprises active compounds (A) and (B) in a weight ratio of from 100:1 to 1:100.

14. A herbicide-safener combination as claimed in claim 11 which additionally comprises formulation auxiliaries.

15. A method for protecting crop plants against phytotoxic side-effects of a herbicide (A), which comprises application of an amount, acting as an antidote, of one or more safeners (B) before, after or simultaneous with the application of herbicide (A) to the plants, parts of plants, plant seeds or the area under cultivation, the herbicide (A) and safener (B) as claimed in claim 1.

16. A method for selective control of weeds in crops of useful plants which comprises applying an herbicidally effective amount of one or more herbicides (A) and an crop-safening effective amount of one or more safeners (B) before, after or simultaneous with the application of herbicide (A) to the plants, parts of plants, plant seeds or the area under cultivation, herbicide (A) and safener (B) claimed in 1.

17. A method for protecting crop plants against phytotoxic side-effects of the herbicide dicamba or salts thereof, which comprises application of an amount, acting as an antidote, of mefenpyr-diethyl before, after or simultaneously with the application of dicamba to the plants, parts of plants, plant seeds or the area under cultivation.

18. A method for selective control of weeds in crops of useful plants which comprises applying an herbicidally effective amount of dicamba or salts thereof and an crop-safening effective amount of mefenpyr-diethyl to the plants, parts of plants, plant seeds or the area under cultivation.

19. A herbicide-safener combination as claimed in claim 1 which comprises as component (B), one or more safeners selected from the group consisting of
(B1.1) compounds of the phenylpyrazolin-3-carboxylic acid type of the formula (I):

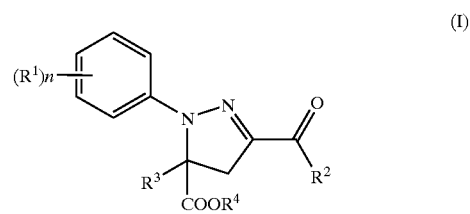

(I)

in which
$R^1$ are identical or different and are halogen, $(C_1-C_4)$-alkyl, $(C_1-C_4)$-alkoxy, nitro or $(C_1-C_4)$-haloalkyl,
n is an integer from 0 to 5,
$R^2$ is $OR^5$, $SR^6$ or $NR^7R^8$ or a saturated or unsaturated 3- to 7-membered heterocycle having at least one nitrogen atom and up to 3 heteroatoms consisting of O and S, which is attached to the carbonyl group in formula (I) via the nitrogen atom and which is unsubstituted or substituted by radicals selected from the group consisting of $(C_1-C_4)$-alkyl, $(C_1-C_4)$-alkoxy and unsubstituted or substituted phenyl,
$R^3$ is hydrogen, $(C_1-C_8)$-alkyl, $(C_1-C_8)$-haloalkyl, $(C_3-C_{12})$-cycloalkyl or substituted or unsubstituted phenyl and
$R^4$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkyl-silyl, and
$R^5$, $R^6$, $R^7$ independently of one another are hydrogen or an unsubstituted or substituted aliphatic hydrocarbon radical, and
$R^8$ is hydrogen, $(C_1-C_6)$-alkyl, $(C_1-C_6)$-alkoxy or substituted or unsubstituted phenyl, and
(B3.2) acylsulfamoylbenzamides of the formula (VI), if appropriate also in salt form,

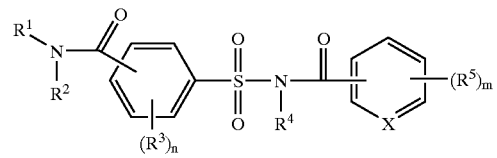

(VI)

in which
X is CH or N,
$R^1$ is hydrogen, heterocyclyl or a hydrocarbon radical, where the two last-mentioned radicals are unsubstituted or substituted by one or more identical or different radicals selected from the group consisting of halogen, cyano, nitro, amino, hydroxyl, carboxyl, CHO, $CONH_2$, $SO_2NH_2$ and $Z^d$-$R^d$,
$R^2$ is hydrogen, hydroxyl, $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, where the five last-mentioned radicals are unsubstituted or substituted by one or more identical or different radicals selected from the group consisting of halogen, hydroxyl, $(C_1-C_4$-alkyl, $(C_1-C_4)$-alkoxy and $(C_1-C_4)$-alkylthio, or
$R^1$ and $R^2$ together with the nitrogen atom that carries them are a 3- to 8-membered saturated or unsaturated ring, $R^3$ are identical or different and are halogen, cyano, nitro, amino, hydroxyl, carboxyl, CHO, $CONH_2$, $SO_2NH_2$ or $Z^e\text{-}R^e$, $R^4$ is hydrogen, $(C_1\text{-}C_4)$-alkyl, $(C_2\text{-}C_4)$-alkenyl or $(C_2\text{-}C_4)$-alkynyl, $R^5$ are identical or different and are halogen, cyano, nitro, amino, hydroxyl, carboxyl, phosphoryl, CHO, $CONH_2$, $SO_2NH_2$ or $Z^f\text{-}R^f$, $R^d$ is a $(C_2\text{-}C_{20})$-alkyl radical whose carbon chain is interrupted once or a plurality of times by oxygen atoms, is heterocyclyl or a hydrocarbon radical, where the two last-mentioned radicals are unsubstituted or substituted by one or more identical or different radicals selected from the group consisting of halogen, cyano, nitro, amino, hydroxy, mono- and di-$[(C_1\text{-}C_4)$-alkyl]amino;

$R^e$, $R^f$ are identical or different and are a $(C_2\text{-}C_{20})$-alkyl radical whose carbon chain is interrupted once or a plurality of times by oxgen atoms, or are heterocyclyl or a hydrocarbon radical, where the two last-mentioned radicals are unsubstituted or substituted by one or more identical or different radicals selected from the group consisting of halogen, cyano, nitro, amino, hydroxyl, phosphoryl, $(C_1\text{-}C_4)$-haloalkoxy, mono- and di-$[(C_1\text{-}C_4)$-alkyl]amino, $Z^d$ is a divalent unit selected from the group consisting of O, S, CO, CS, C(O)O, C(O)S, SO, $SO_2$, NR*, C(O)NR* and $SO_2$NR*, $Z^e$, $Z^f$ are identical or different and are a direct bond or a divalent unit selected from the group consisting of O, S, CO, CS, C(O)O, C(O)S, SO, $SO_2$, NR*, $SO_2$NR* and C(O)NR*, R* is hydrogen, $(C_1\text{-}C_4)$-alkyl or $(C_1\text{-}C_4)$-haloalkyl, n is an integer from 0 to 4, and m is, in the case that X is CH, an integer from 0 to 5 and, in the case that X is N, an integer from 0 to 4.

\* \* \* \* \*